United States Patent
Mason

(10) Patent No.: US 10,836,838 B2
(45) Date of Patent: Nov. 17, 2020

(54) PROCESS AND APPARATUS FOR MANUFACTURING SUGAR ACID

(71) Applicant: METSON MANUFACTURING CC, Johannesburg (ZA)

(72) Inventor: Tom Edgecombe Mason, Johannesburg (ZA)

(73) Assignee: METSON MANUFACTURING CC, Johannesburg (ZA)

( * ) Notice: Subject to any disclaimer, the term of this patent is extended or adjusted under 35 U.S.C. 154(b) by 330 days.

(21) Appl. No.: 15/763,581

(22) PCT Filed: Sep. 27, 2016

(86) PCT No.: PCT/IB2016/055765
§ 371 (c)(1),
(2) Date: Mar. 27, 2018

(87) PCT Pub. No.: WO2017/055993
PCT Pub. Date: Apr. 6, 2017

(65) Prior Publication Data
US 2019/0048100 A1    Feb. 14, 2019

(30) Foreign Application Priority Data

Sep. 28, 2015 (ZA) ................. 2015/07167

(51) Int. Cl.
| | |
|---|---|
| *C08B 31/06* | (2006.01) |
| *A01N 25/02* | (2006.01) |
| *C07C 51/27* | (2006.01) |
| *A01N 57/20* | (2006.01) |
| *C07C 59/255* | (2006.01) |
| *C07C 55/06* | (2006.01) |

(52) U.S. Cl.
CPC .............. *C08B 31/06* (2013.01); *A01N 25/02* (2013.01); *A01N 57/20* (2013.01); *C07C 51/27* (2013.01); *C07C 55/06* (2013.01); *C07C 59/255* (2013.01)

(58) Field of Classification Search
None
See application file for complete search history.

(56) References Cited

U.S. PATENT DOCUMENTS

| | | | | |
|---|---|---|---|---|
| 2,112,989 A | * | 4/1938 | Helle | ...................... C08B 31/06 536/48 |
| 2,380,196 A | | 7/1945 | Soltzberg | |
| 2,995,549 A | | 8/1961 | Zimmermann et al. | |
| 3,456,357 A | | 7/1969 | Griffith | |
| 5,849,356 A | * | 12/1998 | Gambino | ............... C09K 3/185 427/136 |
| 2001/0051591 A1 | * | 12/2001 | Ferrett | ............... A01N 2300/00 504/103 |

FOREIGN PATENT DOCUMENTS

| | | |
|---|---|---|
| CN | 101311240 A | 11/2008 |
| CN | 101434623 A | 5/2009 |

OTHER PUBLICATIONS

Anonymous, "Scrubber." Wikipedia, Feb. 2018 [retrieved on Mar. 28, 2018], Retrieved from the Internet: <URL: https://en.wikipedia.org/wiki/Scrubber>.

* cited by examiner

*Primary Examiner* — Monica A Shin
(74) *Attorney, Agent, or Firm* — Saliwanchik, Lloyd & Eisenschenk

(57) ABSTRACT

The present invention relates to a novel process for manufacturing a sugar acid for the use in the agricultural market as an adjuvant wherein the process includes the following steps of providing a reactor and introducing a source of nitric acid, water and a source of starch into the reactor to form a mixture and further includes introducing an external heat source to the mixture to ascertain a mixture temperature of at least 70° C. and discontinuing the external heat source once the mixture reaches about 70° C.; and further enabling an internal heat source in the form of an exothermic reaction to occur between the reagents for at least two (2) hours. The invention also relates to the use of the product as obtained from the process.

7 Claims, 5 Drawing Sheets

PROCESS AND APPARATUS FOR MANUFACTURING SUGAR ACID

CROSS REFERENCE TO RELATED APPLICATIONS

This application is a National Stage Application of International Application Number PCT/IB2016/055765, filed Sep. 27, 2016; which claims priority to South Africa Application No. 2015/07167, filed Sep. 28, 2015.

TECHNICAL FIELD

The present invention relates to a novel process and apparatus for manufacturing sugar acid for use in the agricultural market as an adjuvant to be used in conjunction with a pesticide.

BACKGROUND TO THE INVENTION

Conventionally, agricultural spray adjuvants are used to enhance the effectiveness of pesticides such as herbicides, insecticides, fungicides and other agents that control or eliminate unwanted pests. In addition, these additives modify certain properties, which in turn improve the ability of the pesticide to penetrate, target or protect the target organism. Among the typical types of ingredients used are surfactants, emulsifiers, oils and salts.

An intermediary product called a sugar acid is produced by reacting corn starch with nitric acid at an elevated temperature and at standard atmospheric pressure. Sugar acid, also called nitro-starch, can be described as a mixture of various nitric acid esters of starch with different degrees of nitration. When heated to decomposition, sugar acid emits toxic fumes of NOx.

Early industrial sugar acid production was often carried out through the reaction of starch with mineral acid. These reactions are typically run at high temperatures and pressure with only catalytic amounts of acid.

The intention of such reactions is to fully hydrolyze the alpha 1-4 and alpha 1-6 glycosidic bonds that make up the starch polymer. The result is a complex mixture of varied sized glucose oligomers.

The main disadvantage associated with the aforesaid conventional processes for the production of sugar acids, produced under pressure with only catalytic amounts of acid, is the production of a high degree of hydrolyzation during said sugar acid formation.

Yet another disadvantage associated with conventional sugar acid production is the lack of excess un-reacted $HNO_3$ being part of the final resultant product.

Another disadvantage identified in the prior art is the lack of multiple heating sources employed in conjunction with each other for efficient heating during production.

In view of the foregoing discussion, it is apparent that there is a need in the art for providing a novel process and resultant product for use as an adjuvant to addresses the shortcomings and/or disadvantages identified above.

SUMMARY OF THE INVENTION

According to a first aspect thereof, the present invention provides a process for the production of sugar acid for use in the agricultural market as an adjuvant, said process including the following steps:

(i) providing a reactor;
(ii) introducing a source of nitric acid, water and a source of starch into the reactor to form a mixture;
(iii) introducing an external heat source to the mixture to ascertain a mixture temperature of at least 70° C.;
(iv) discontinuing the external heat source once the mixture reaches about 70° C.; and
(v) enabling an internal heat source in the form of an exothermic reaction to occur between the reagents for at least 2 hours.

In a preferred embodiment of the invention, the starting ratio of the mixture may include 200 kg to 400 kg of water per 750 litre mixture.

The starting ratio may include 130 litres to 330 litres of nitric acid at a concentration of 9.7 M per 750 litre mixture.

The starting ratio may include 150 kg to 290 kg of starch per 750 litre mixture.

The present invention does not teach of a preferred sequence for the addition of the starting reagents and therefore the reagents may be added in any sequence of order.

There is further provided for the source of starch to be corn (maize) starch.

Optionally, the introduction of additional water may occur after step (v), to provide for a total volume of 750 litres at the end of the process as evaporation may cause the loss of water during production.

There is provided for using reagent grade nitric acid which may be available at 55-70% strength (m/m).

In an exemplary embodiment, there is provided for the use of 198 litres of the nitric acid having 1.42 grams/millilitre at 15° C., which relates to a mass of 281.2 kg of acid added per 750 litre batch.

The molarity of the source of nitric acid may be 15.78 moles/litre.

The nitric acid molarity in 750 litres of reagent with the source of starch added before the reaction takes place may be 4.17 moles/litre.

A further feature of the invention is that the total mass percentage of nitric acid before the reaction occurs may be 21.44%.

A still further feature provides that during the reaction, the initiation of nitration takes place only once heat is added during step (iii) of the above reaction whereupon the reaction may be exothermic and mostly self-perpetuating as long as sufficient nitric acid is present to enable the exothermic reaction.

A yet further feature may be that approximately 65% to 70% of the nitric acid is consumed during the reaction, with most of the acid left in the final product being "affixed" ester-nitrates, which may explain the slow-down of the reaction after approximately 2 hours, followed by slow cooling.

There is further provided for the process to include the use of atomised water to absorb the gas emissions being produced during said reaction.

In a preferred embodiment, filtration of the resultant product may also occur at a later stage due to the formation of a white sediment.

In yet another embodiment, multiple batches of the resultant product may be pooled.

In another embodiment of the invention, additional post production testing may be done to determine the total un-reacted acid, post production.

According to a second aspect thereof, the present invention provides a reactor for the production of sugar acid, in the process as defined herein above, for use in the agricultural market as an adjuvant, said reactor including:

(i) a vessel having at least one opening for containing a mixture of a source of nitric acid, a source of water and a source of starch;
(ii) a lid for closing the at least one opening of the vessel;
(iii) at least two independent heat sources for heating the mixture;
(iv) at least one stirrer for stirring the mixture; and
(v) at least one scrubbing device connected to the vessel for removing gas emissions resulting from chemical reactions within the mixture.

In an embodiment of the present invention, the at least two independent heat sources for heating the mixture may be in the form of a heating jacket positioned around the vessel and heating elements positioned directly into the mixture for speeding up the heating process.

In a preferred embodiment of the invention, the at least one stirrer may include a motor, gearbox, shaft and propeller, wherein the shaft and propeller protrudes into the vessel for mixing the mixture during production.

In another embodiment, at least one scrubbing device may be capable of cleaning the gas emissions produced from the process herein above. At least one scrubbing device may further be a wet scrubbing device. The wet scrubbing device may include a fan that draws the gas from the reaction. The wet scrubbing device may further employ the use of atomised water to absorb the gas emissions produced. In addition, the wet scrubbing device may include the use of caustic soda in combination with the atomised water.

According to a third aspect thereof, the present invention provides for a sugar acid product, as obtained from the process described herein above, for use in the agricultural market as an adjuvant.

In one embodiment of the invention, the final product as obtained herein above may contain at least 1 molar of un-reacted acid post production in the aforementioned process as described.

In a preferred embodiment, the nitrogen analysis of the product may contain at least 6 g/kg of nitrogen. In yet another embodiment, the remaining un-reacted nitrogen may be in the form of $HNO_3$, and may indicate that at least 20% of the total added nitric acid still remains in the final product, post production.

A non-limiting example of the product's density may be 1.1194 kg/litre.

Another example is that the product may have 11.08 g/litre of nitrogen.

According to a fourth aspect thereof, the present invention provides use of the product in combination with glyphosate.

According to a fifth aspect thereof, the present invention provides for a composition including the product in combination with glyphosate and cations for enhancing the uptake and/or efficacy of glyphosate. In one embodiment of the invention the cations may be $CaCl_2$.

According to a sixth aspect thereof, the present invention provides use of the product or the composition in the manufacture of a herbicide for administration to a plant.

According to a seventh aspect thereof, the present invention provides for the use of the product or the composition as a carrier for ions such as iron, calcium, copper, manganese or the like, in the manufacture of a herbicide, due to the multivalent nature of the anionicity of the final product.

According to an eighth aspect thereof, the present invention provides a means of characterizing the product herein described, by LC-MS results showing the distribution of the moieties as shown in FIGS. 5 and 6 and in Table 5.

These and other objects, features and advantages of the invention will become apparent to those skilled in the art in the following detailed description of the invention.

The presently disclosed subject matter will now be described more fully hereinafter with reference to the accompanying examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

DESCRIPTION OF THE INVENTION

Figure 1:
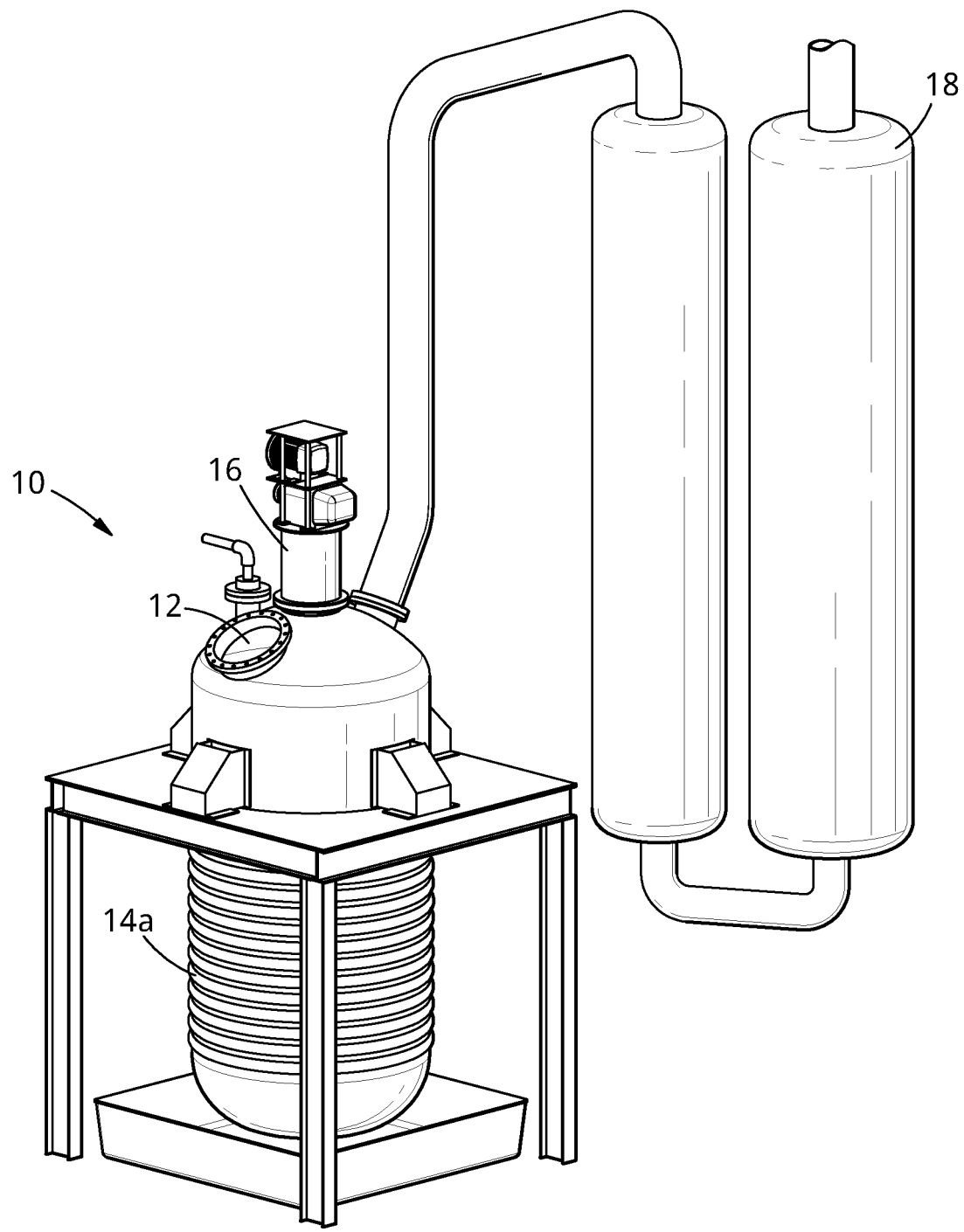
FIG. 1: shows a perspective view of the apparatus of the present invention.

FIG. 1 shows a vessel (10) having at least one opening (12) and a lid (not shown) for closing the at least one opening (12) of the vessel (10). The vessel (10) further includes at least two independent heat sources (14a and 14b) for heating the mixture and at least one stirrer (16). The vessel (10) also includes at least one scrubbing device (18) connected to the vessel (10) for removing gas emissions resulting from chemical reactions within the vessel (10).

FIG. 1 further show that the vessel (10) is in the form of a reactor (10). The at least two independent heat sources are in the form of a heating jacket (14a) positioned around the reactor (10) and heating elements (14b)(FIG. 2) positioned directly into a mixture for speeding up the heating process.

Figure 2:
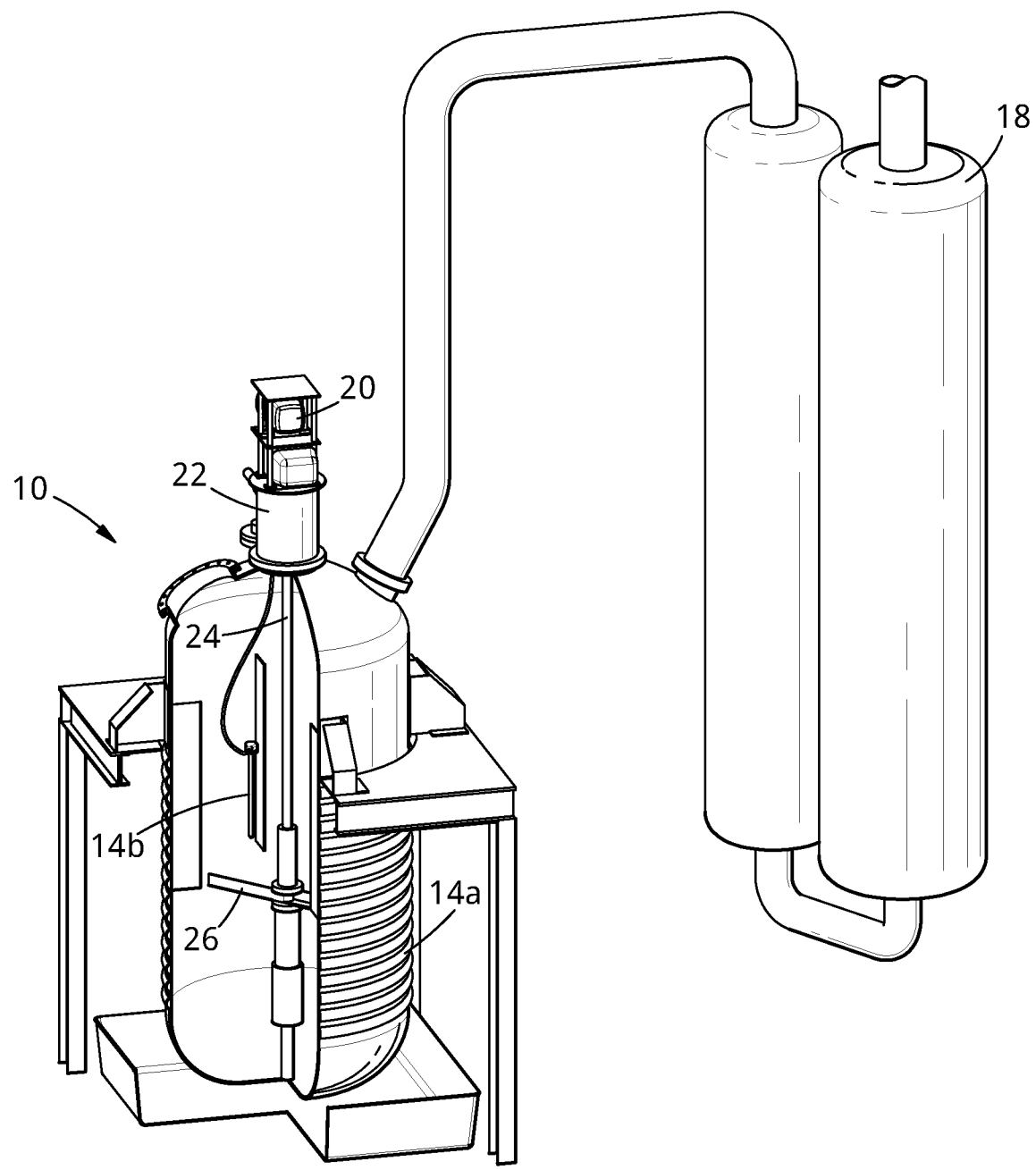
FIG. 2: depicts yet another perspective view of the apparatus of the present invention having a cut out section.
Figure 3:
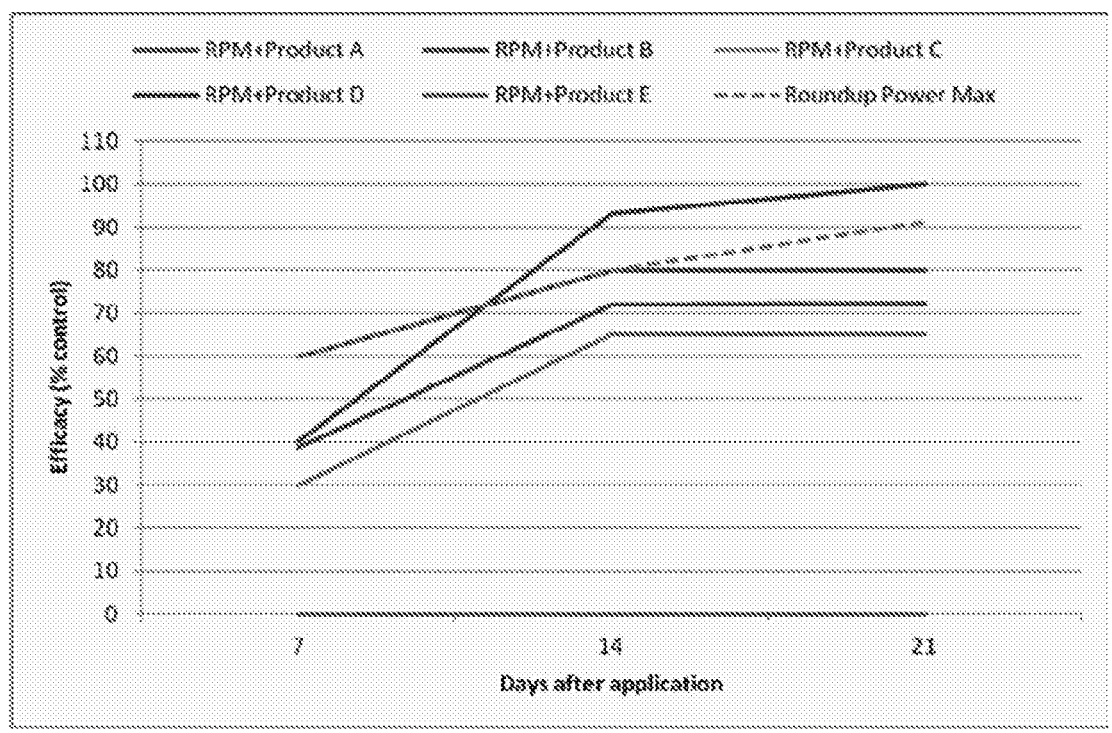
FIG. 3: depicts the efficacy of different adjuvants relevant to days after application.

In FIG. 2, the stirrer (16) includes a motor (20), gearbox (22), shaft (24) and propeller (26), wherein the shaft (24) and propeller (26) protrudes into the reactor (10) for mixing the mixture during production. The at least one scrubbing device (18) is capable of cleaning gas emissions produced inside the reactor (10). The at least one scrubbing device (18) is a wet scrubbing device (18). The wet scrubbing device includes a fan (not shown) that draws the gas from the inside of the reactor (10). The wet scrubbing device (18) employs the use of atomised water to absorb the gas emissions produced. In addition, the wet scrubbing device (18) includes the use of caustic soda in combination with atomised water.

In terms of the process, despite the production of NOx species during the process which suggests the brake down of nitric acid, the large amounts of nitric acid used as well as its catalytic nature in starch hydrolysis strongly suggests a large portion of un-reacted nitric acid should remain in the final product. The amount of un-reacted nitric acid need be accurately known in order to use the sugar acid efficiently in downstream reactions.

In addition, this helps to reduce waste (by not adding excess nitric acid when not necessary) as well as to ensure that downstream products are not too acidic for the end user.

The variable nature of the sugar acid calls for continued batch analysis after several reaction products are collected into large storage tanks.

However, this residual nitric acid only accounts for 46.1% of the total measured acidity. It is very likely that the remaining acidity is attributed to various kinds of weak organic acids formed as oxidation by products, especially terminal carboxylic acid groups.

Moreover, it was noted that on several occasions despite having stopped the reaction the product once transferred to resting containers continues to remain warm and it is believed that the reaction of the internal products of the mixture is not completed during the aforementioned process. This is further validated by the fact that upon resting, the product produces a white settlement. This is most likely un-reacted starch.

In addition, titration with standard sodium hydroxide solution can be used to evaluate the amount of un-reacted nitric acid. This procedure is described below. Since theoretically there can be as much as 14.1% of N in nitro-starch which would correspond to 4 Moles of $NO_3$ reacted with each glucose molecule in the structure, it stands to reason that having approximately ⅔ of that amount of Nitrogen present in the sugar acid product of the present invention, even allowing for a small amount of residual free nitric acid in the reaction solution, there will be between 2 and 3 nitrated sites to each glucose unit in the starch. The discussion herein below will show a surprisingly, unexpected result of improved adjuvant properties due to the excess un-reacted $HNO_3$ as part of the final resultant product.

Example

A 1 M stock solution of sodium hydroxide was made by dissolving 10.0 g NaOH in a 250 ml volumetric flask. The stock solution was standardized with potassium hydrogen phthalate AR in triplicate. Phenolphthalein was used as the indicator after dissolving the KHPhthalate in 150 ml distilled (d) water ($H_2O$).

The sugar acid (10 ml) sample was added to 100 ml $dH_2O$ and the solution titrated with the standardized NaOH solution. A calibrated pH meter was used to determine the end point (pH=7.0). A non-limiting example of the neutralization may show that the concentration of un-reacted $HNO_3$ is 1.71 M. It is further recommended to use a pH meter to detect the end point using pH=7.0 as the marker of equivalence.

Product Testing:

In terms of the product obtained from the aforesaid process, the efficacy of said product was determined by comparing different adjuvants in combination with glyphosate on various weed species in a glasshouse. Table 1 shows the various treatments of different adjuvants in combination with glyphosate and Table 2 shows the pH values for mixing of the different adjuvants with Roundup PowerMax™ (glyphosate) in water.

TABLE 1

Various treatments of different adjuvants in combination with glyphosate

| TMT no | Herbicide | Dosage l/ha | MSO | Dosage ml/l |
|---|---|---|---|---|
| 1 | Roundup PowerMax ™ | 1.7 | Product A (Express 50082) B + Molite | 20 |
| 2 | 540 g ai/L SL | | Product B (Express 50084) Soya Ultra | 20 |
| 3 | | | Product C (Express 50083) Funatiomr | 20 |
| 4 | | | Product D (The sugar acid of the present invention). | 0.5 |
| 5 | | | Product E ZMC | 20 |
| 6 | | | None | 20 |
| 7 | Control | — | None | — |

TABLE 2 pH values for mixing of adjuvants and Roundup PowerMax ™ in water

| Treatments | Water + Product | Water + Bladbuff | Water + Bladbuff + Product | Water + Bladbuff + Product + |
|---|---|---|---|---|
| Product A (Express 50082) B + Molite | 8.33 | 5.93 | 5.11 | 6.58 |
| Product B (Express 50084) Soya Ultra | 7.74 | 5.73 | 6.26 | 4.93 |
| Product C (Express 50083) | 4.90 | 5.80 | 4.73 | 4.52 |
| Product D (The sugar acid of the present invention) | 7.07 | 5.53 | 4.67 | 4.62 |
| Product E ZMC | 4.92 | 5.38 | 4.60 | 4.43 |

Glasshouse trial was conducted where clay loam top soil (36% clay) was placed into rectangular plastic containers measuring 320 mm×445 mm×90 mm. Soil was collected from a field where maize is produced and summer annual weed species occurred, ensuring a weed seedbank. Containers were watered daily to accommodate emergence of naturally occurring weed species.

The following weed species emerged, *Amaranthus hybridus* (Common pigweed), *Emex australis* (Devil's thorn) and *Datura ferox* (Large thorn apple). Although day length and temperature were controlled in the glasshouse, few weed species emerged successfully and may be ascribed to seed dormancy. The experimental layout was a complete randomised block design with four replicates per treatment. Holes at the bottom of each container allowed for free drainage. Chemicult fertilizer was applied to each container (±200 ml) two weeks after emergence of weed seedlings.

Growing conditions maintained in the glasshouse were 15/30° C., and 10/14 h (night/day; dark/light) for the duration of the trial. Herbicide treatments were applied when most of the weed seedlings had four leaves fully unfolded. The herbicide treatments were applied to the soil surface one day after planting of seed using a $CO_2$ powered conveyer-band sprayer fitted with one TeeJet 8004E band nozzle delivering a volume of 250 l·ha$^{-1}$ at 200 kPa. Control treatments received no herbicide or adjuvant applications.

The pH of mixing water was 7.3 and the buffer Bladbuff was added to water to adjust the pH for mixing with Roundup PowerMax™ (as per label instructions). Only hygroboost (ammonium sulphate) was added to the Roundup PowerMax™ (Treatment 6) as per label instructions. The pH values after MSO (Products A, B, C, D and E) addition followed by Roundup PowerMax™ is shown in Table 2.

The trial consisted of seven treatments (control treatments included, see Table 1). Bladbuff was added to mixing water to stabilize the pH of treatments 1 to 6 at 5. The relevant adjuvants were then added to the respective water samples at 2% concentration, followed by glyphosate (Roundup PowerMax™) to a dosage rate of 1.7 l·ha$^{-1}$.

Visual evaluations, where the percentage of necrosis of each treatment were recorded and compared to control treatments, were done on 7, 14 and 21 days after application (DAA) and are shown in Table 3.

TABLE 3

Control of weed seedlings where 7 treatments with Roundup PowerMax™ alone or in combination with 5 adjuvants, i.e. Product A, B, C, D and E, was applied post emergence, respectively

| Treatments | DAA* | Rep | Amaranthus hybridus (%) | Datura ferox (%) | Control (% mean) |
|---|---|---|---|---|---|
| Roundup PowerMax™ + Product A | 7 | 1 | 0.00 | 30.00 | 15.00 |
| Roundup PowerMax™ + Product A | 7 | 2 | 0.00 | 50.00 | 25.00 |
| Roundup PowerMax™ + Product A | 7 | 3 | 100.00 | 50.00 | 75.00 |
| Roundup PowerMax™ + Product A | 7 | 4 | 50.00 | 30.00 | 40.00 |
| | | Mean | 37.50 | 40.00 | 38.75 |
| Roundup PowerMax™ + Product B | 7 | 1 | 100.00 | 10.00 | 55.00 |
| Roundup PowerMax™ + Product B | 7 | 2 | 100.00 | 10.00 | 55.00 |
| Roundup PowerMax™ + Product B | 7 | 3 | 100.00 | 10.00 | 55.00 |
| Roundup PowerMax™ + Product B | 7 | 4 | 100.00 | 50.00 | 75.00 |
| | | Mean | 100.00 | 20.00 | 60.00 |
| Roundup PowerMax™ + Product C | 7 | 1 | 100.00 | 10.00 | 55.00 |
| Roundup PowerMax™ + Product C | 7 | 2 | 0.00 | 10.00 | 5.00 |
| Roundup PowerMax™ + Product C | 7 | 3 | 0.00 | 10.00 | 5.00 |
| Roundup PowerMax™ + Product C | 7 | 4 | 100.00 | 10.00 | 55.00 |
| | | Mean | 50.00 | 10.00 | 30.00 |
| Roundup PowerMax™ + Product D | 7 | 1 | 100.00 | 10.00 | 55.00 |
| Roundup PowerMax™ + Product D | 7 | 2 | 100.00 | 50.00 | 75.00 |
| Roundup PowerMax™ + Product D | 7 | 3 | 0.00 | 10.00 | 5.00 |
| Roundup PowerMax™ + Product D | 7 | 4 | 0.00 | 50.00 | 25.00 |
| | | Mean | 50.00 | 30.00 | 40.00 |
| Roundup PowerMax™ + Product E | 7 | 1 | 0.00 | 0.00 | 0.00 |
| Roundup PowerMax™ + Product E | 7 | 2 | 0.00 | 0.00 | 0.00 |
| Roundup PowerMax™ + Product E | 7 | 3 | 0.00 | 0.00 | 0.00 |
| Roundup PowerMax™ + Product E | 7 | 4 | 0.00 | 0.00 | 0.00 |
| | | Mean | 0.00 | 0.00 | 0.00 |
| Roundup PowerMax™ | 7 | 1 | 100.00 | 20.00 | 60.00 |
| Roundup PowerMax™ | 7 | 2 | 100.00 | 10.00 | 55.00 |
| Roundup PowerMax™ | 7 | 3 | 0.00 | 100.00 | 50.00 |
| Roundup PowerMax™ | 7 | 4 | 100.00 | 50.00 | 75.00 |
| | | Mean | 75.00 | 45.00 | 60.00 |
| Control | 7 | 1 | 0 | 0 | 0 |
| Control | 7 | 2 | 0 | 0 | 0 |
| Control | 7 | 3 | 0 | 0 | 0 |
| Control | 7 | 4 | 0 | 0 | 0 |
| | | Mean | 0 | 0 | 0 |
| Roundup PowerMax™ + Product A | 14 | 1 | 50.00 | 50.00 | 50.00 |
| Roundup PowerMax™ + Product A | 14 | 2 | 100.00 | 50.00 | 75.00 |
| Roundup PowerMax™ + Product A | 14 | 3 | 100.00 | 80.00 | 90.00 |
| Roundup PowerMax™ + Product A | 14 | 4 | 50.00 | 95.00 | 72.50 |
| | | Mean | 75.00 | 68.75 | 71.88 |
| Roundup PowerMax™ + Product B | 14 | 1 | 50.00 | 50.00 | 50.00 |
| Roundup PowerMax™ + Product B | 14 | 2 | 100.00 | 90.00 | 95.00 |
| Roundup PowerMax™ + Product B | 14 | 3 | 100.00 | 50.00 | 75.00 |
| Roundup PowerMax™ + Product B | 14 | 4 | 100.00 | 100.00 | 100.00 |
| | | Mean | 87.50 | 72.50 | 80.00 |
| Roundup PowerMax™ + Product C | 14 | 1 | 50.00 | 50.00 | 50.00 |
| Roundup PowerMax™ + Product C | 14 | 2 | 50.00 | 80.00 | 65.00 |
| Roundup PowerMax™ + Product C | 14 | 3 | 50.00 | 50.00 | 50.00 |
| Roundup PowerMax™ + Product C | 14 | 4 | 100.00 | 90.00 | 95.00 |
| | | Mean | 62.50 | 67.50 | 65.00 |
| Roundup PowerMax™ + Product D | 14 | 1 | 100.00 | 100.00 | 100.00 |
| Roundup PowerMax™ + Product D | 14 | 2 | 100.00 | 100.00 | 100.00 |

TABLE 3-continued

Control of weed seedlings where 7 treatments with
Roundup PowerMax ™ alone or in combination
with 5 adjuvants, i.e. Product A, B, C, D and E,
was applied post emergence, respectively

| Treatments | DAA* | Rep | Amaranthus hybridus (%) | Datura ferox (%) | Control (% mean) |
|---|---|---|---|---|---|
| Roundup PowerMax ™ + Product D | 14 | 3 | 100.00 | 95.00 | 97.50 |
| Roundup PowerMax ™ + Product D | 14 | 4 | 50.00 | 100.00 | 75.00 |
| | | Mean | 87.50 | 98.75 | 93.13 |
| Roundup PowerMax ™ + Product E | 14 | 1 | 0.00 | 0.00 | 0.00 |
| Roundup PowerMax ™ + Product E | 14 | 2 | 0.00 | 0.00 | 0.00 |
| Roundup PowerMax ™ + Product E | 14 | 3 | 0.00 | 0.00 | 0.00 |
| Roundup PowerMax ™ + Product E | 14 | 4 | 0.00 | 0.00 | 0.00 |
| | | Mean | 0.00 | 0.00 | 0.00 |
| Roundup PowerMax ™ | 14 | 1 | 50.00 | 100.00 | 75.00 |
| Roundup PowerMax ™ | 14 | 2 | 50.00 | 90.00 | 70.00 |
| Roundup PowerMax ™ | 14 | 3 | 50.00 | 100.00 | 75.00 |
| Roundup PowerMax ™ | 14 | 4 | 100.00 | 100.00 | 100.00 |
| | | Mean | 62.50 | 97.50 | 80.00 |
| Control | 14 | 1 | 0 | 0 | 0 |
| Control | 14 | 2 | 0 | 0 | 0 |
| Control | 14 | 3 | 0 | 0 | 0 |
| Control | 14 | 4 | 0 | 0 | 0 |
| | | Mean | 0 | 0 | 0 |
| Roundup PowerMax ™ + Product A | 21 | 1 | 50.00 | 50.00 | 50.00 |
| Roundup PowerMax ™ + Product A | 21 | 2 | 100.00 | 50.00 | 75.00 |
| Roundup PowerMax ™ + Product A | 21 | 3 | 100.00 | 80.00 | 90.00 |
| Roundup PowerMax ™ + Product A | 21 | 4 | 50.00 | 99.00 | 74.50 |
| | | Mean | 75.00 | 69.75 | 72.38 |
| Roundup PowerMax ™ + Product B | 21 | 1 | 50.00 | 50.00 | 50.00 |
| Roundup PowerMax ™ + Product B | 21 | 2 | 100.00 | 90.00 | 95.00 |
| Roundup PowerMax ™ + Product B | 21 | 3 | 100.00 | 50.00 | 75.00 |
| Roundup PowerMax ™ + Product B | 21 | 4 | 100.00 | 100.00 | 100.00 |
| | | Mean | 87.50 | 72.50 | 80.00 |
| Roundup PowerMax ™ + Product C | 21 | 1 | 50.00 | 50.00 | 50.00 |
| Roundup PowerMax ™ + Product C | 21 | 2 | 50.00 | 80.00 | 65.00 |
| Roundup PowerMax ™ + Product C | 21 | 3 | 50.00 | 50.00 | 50.00 |
| Roundup PowerMax ™ + Product C | 21 | 4 | 100.00 | 90.00 | 95.00 |
| | | Mean | 62.50 | 67.50 | 65.00 |
| Roundup PowerMax ™ + Product D | 21 | 1 | 100.00 | 100.00 | 100.00 |
| Roundup PowerMax ™ + Product D | 21 | 2 | 100.00 | 100.00 | 100.00 |
| Roundup PowerMax ™ + Product D | 21 | 3 | 100.00 | 100.00 | 100.00 |
| Roundup PowerMax ™ + Product D | 21 | 4 | 100.00 | 100.00 | 100.00 |
| | | Mean | 100.00 | 100.00 | 100.00 |
| Roundup PowerMax ™ + Product E | 21 | 1 | 0.00 | 0.00 | 0.00 |
| Roundup PowerMax ™ + Product E | 21 | 2 | 0.00 | 0.00 | 0.00 |
| Roundup PowerMax ™ + Product E | 21 | 3 | 0.00 | 0.00 | 0.00 |
| Roundup PowerMax ™ + Product E | 21 | 4 | 0.00 | 0.00 | 0.00 |
| | | Mean | 0.00 | 0.00 | 0.00 |
| Roundup PowerMax ™ | 21 | 1 | 80.00 | 100.00 | 90.00 |
| Roundup PowerMax ™ | 21 | 2 | 80.00 | 90.00 | 85.00 |
| Roundup PowerMax ™ | 21 | 3 | 80.00 | 100.00 | 90.00 |
| Roundup PowerMax ™ | 21 | 4 | 100.00 | 100.00 | 100.00 |
| | | Mean | 85.00 | 97.50 | 91.25 |
| Control | 14 | 1 | 0 | 0 | 0 |
| Control | 14 | 2 | 0 | 0 | 0 |
| Control | 14 | 3 | 0 | 0 | 0 |
| Control | 14 | 4 | 0 | 0 | 0 |
| | | Mean | 0 | 0 | 0 |

*DAA = Days after application

Data were subjected to an ANOVA to compare treatments at the 5% significance level to determine efficacy of products using Genstat® for Windows version 5.

In terms of results, the first symptoms were observed 6 DAA in the Roundup PowerMax™ and Roundup PowerMax™+Product B treatments followed by the Roundup PowerMax™+Product D. *A. hybridus* wilted first followed by *D. ferox*. *E. australis* did not show significant symptoms and was never completely controlled. Roundup PowerMax™+Product E showed no symptoms from application until completion of the trial. Roundup PowerMax™+Product A and Roundup PowerMax™+Product C showed poor control on all weed species (72% and 65%, respectively).

Figure 4:
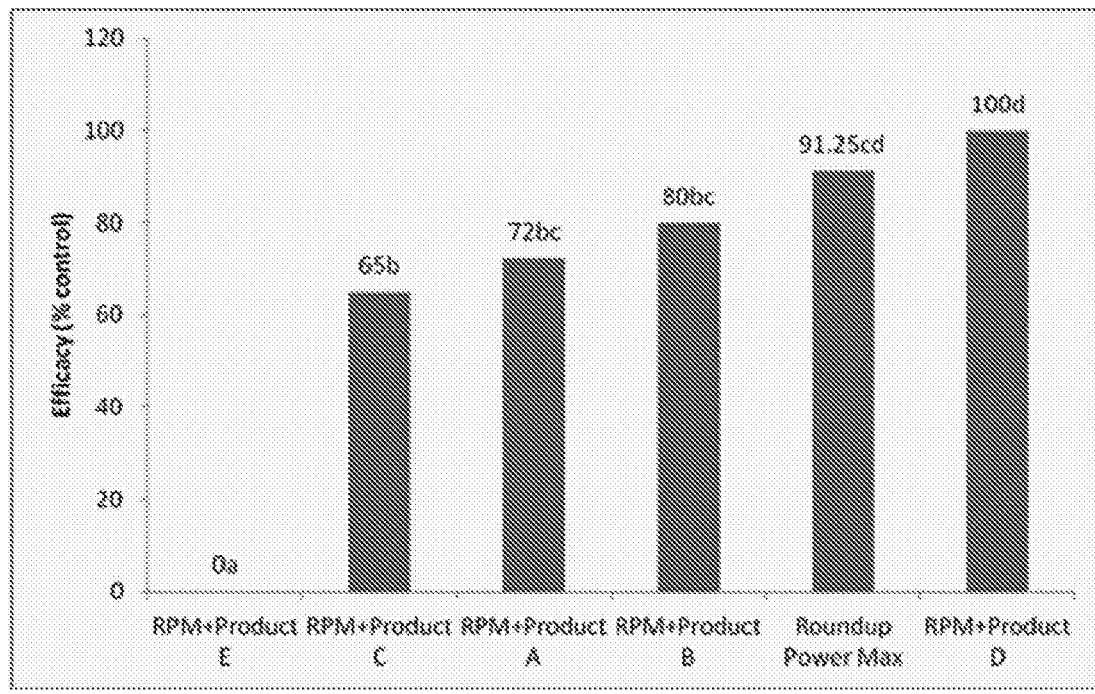
FIG. 4: depicts percentage control at 21 days after application for different adjuvants.

Roundup Power Max™ and Roundup PowerMax™+Product B showed 60% of wilting 7 DAA. At 14 DAA all treatments (except with Product E) showed wilting of >65%. On 21 DAA, only Roundup Power Max™, Roundup PowerMax™+Product B and Roundup PowerMax™+Product D showed effective control (>80%). Roundup PowerMax™+ Product A and Roundup PowerMax™+Product C, only controlled weeds 72% and 65%, respectively at 21 DAA. The difference in weed control between all treatments at 21 DAA can be seen in FIG. 4.

In addition, it is worth mentioning that Products A and E showed severe precipitation after Roundup PowerMax™ was added to the mixture. Products B and C showed less precipitation and Product D was clear.

In terms of a conclusion, the addition of products A, B, and C to Roundup PowerMax™ did not enhance the efficacy of the herbicide significantly and provided only suppressed or reduced control (between 50-80%) when mixed with Roundup PowerMax™. Only the addition of Product D (the product of the instant process) enhanced the efficacy of Roundup PowerMax with 9%.

Roundup PowerMax™ and Roundup PowerMax™+ Product D gave commercially acceptable weed control at 21 DAA (>90%). Product E is not compatible with Roundup PowerMax™ since no symptoms were observed on the weed spectrum. The respective addition of products A, B, C and E to Roundup Power Max™ resulted in visible precipitation just after mixing. These products seemed to be not compatible with Roundup PowerMax™. The addition of Product D to Roundup PowerMax™ resulted in a clear mixing solution and together with effective control results, is considered to be compatible with Roundup PowerMax™.

Further Testing:

In addition, multiple subsequent tests were performed wherein no visual precipitation or residues were observed for any of the mixtures and all treatments showed a clear solution after mixing the relevant product as described herein with different water hardness concentrations. The pH value of water hardness with $CaCl_2$ was 5.0 and increased to 6.0 at the highest concentration. The pH values for water hardness with NaCl stayed the same at 4.8 regardless of the concentration. Water hardness with $NaHCO_3$ had the highest pH values and varied between 7.6 and 8.9.

The addition of the sugar acid product of the present invention or ammonium sulphate based adjuvant reduced the pH value significantly in the $CaCl_2$ and NaCl treatments. Although the pH has reduced in the $NaHCO_3$ water concentrations the reduction was not as significant. The respective glyphosate treatments, regardless of adjuvants and water hardness did not effectively control *I. purerea, C. benghalensis* and *C. esculentus*. Efficacy was therefore rated twice, once where the overall rating was recored for each treatment at 7, 14 and 21 DAA.

The most effective overall control was recorded for the water+Roundup PowerMax™+ammonium sulphate based adjuvant (80%), with most of the treatments resulting in only less than 70% control (suppressed reduced control). Efficacy differences were very slight but water hardness with $CaCl_2$ and $NaHCO_3$ tend to have a greater effect on efficacy compared to NaCl concentrations. A second rating was also done on weed species that were effectively controlled (*A. hybridus, C. album, C. carinatum, T. minuta, P. oleracea, D. stramonium, D. saguinalis* and *U. panicoides*) at 14 and 21 DAA (Table 4). Effective control (>90%) was achieved for most treatments.

The rest of the weed species prevalent in each treatment were effectively controlled in all treatments at 21 DAA. Efficacy differed very slightly between water hardness treatments and was only observed within the first two weeks after application. There was little difference between the NaCl treatments with or without the sugar acid product described herein, ammonium sulphate based adjuvant or alone. With $NaHCO_3$, weed control with Roundup PowerMax™ alone was 96.4% and with the sugar acid product described herein 98.8%, while with ammonium sulphate based adjuvant it was 99.8% control. With $CaCl_2$, however, Roundup PowerMax™ alone was 92.1% while in combination with the sugar acid product described herein it was 98.2% and with the ammonium sulphate based adjuvant 100%.

In conclusion, the addition of the sugar acid product described herein or with the ammonium sulphate based adjuvant greatly improved the efficiency of Roundup PowerMax™ in the $CaCl_2$ treatments. Roundup PowerMax™ efficiency is more susceptible to $CaCl_2$ than NaCl and $NaHCO_3$. The addition of sugar acid product described herein and ammonium sulphate based adjuvant greatly improved the efficiency of Roundup PowerMax™ in $CaCl_2$ treatments.

Figure 5:
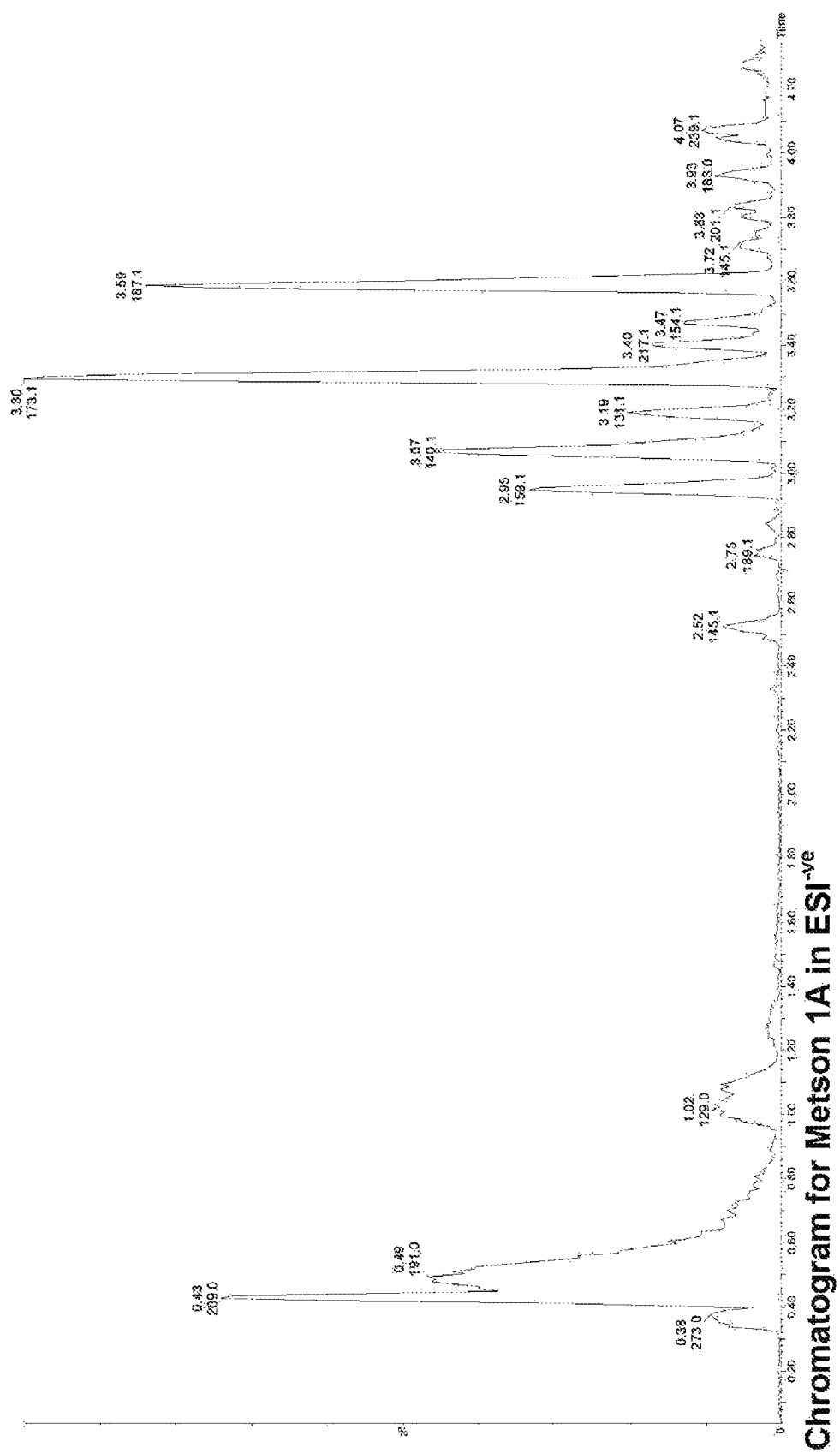
FIG. 5: depicts LC-MS results for the product as described.
Figure 6:
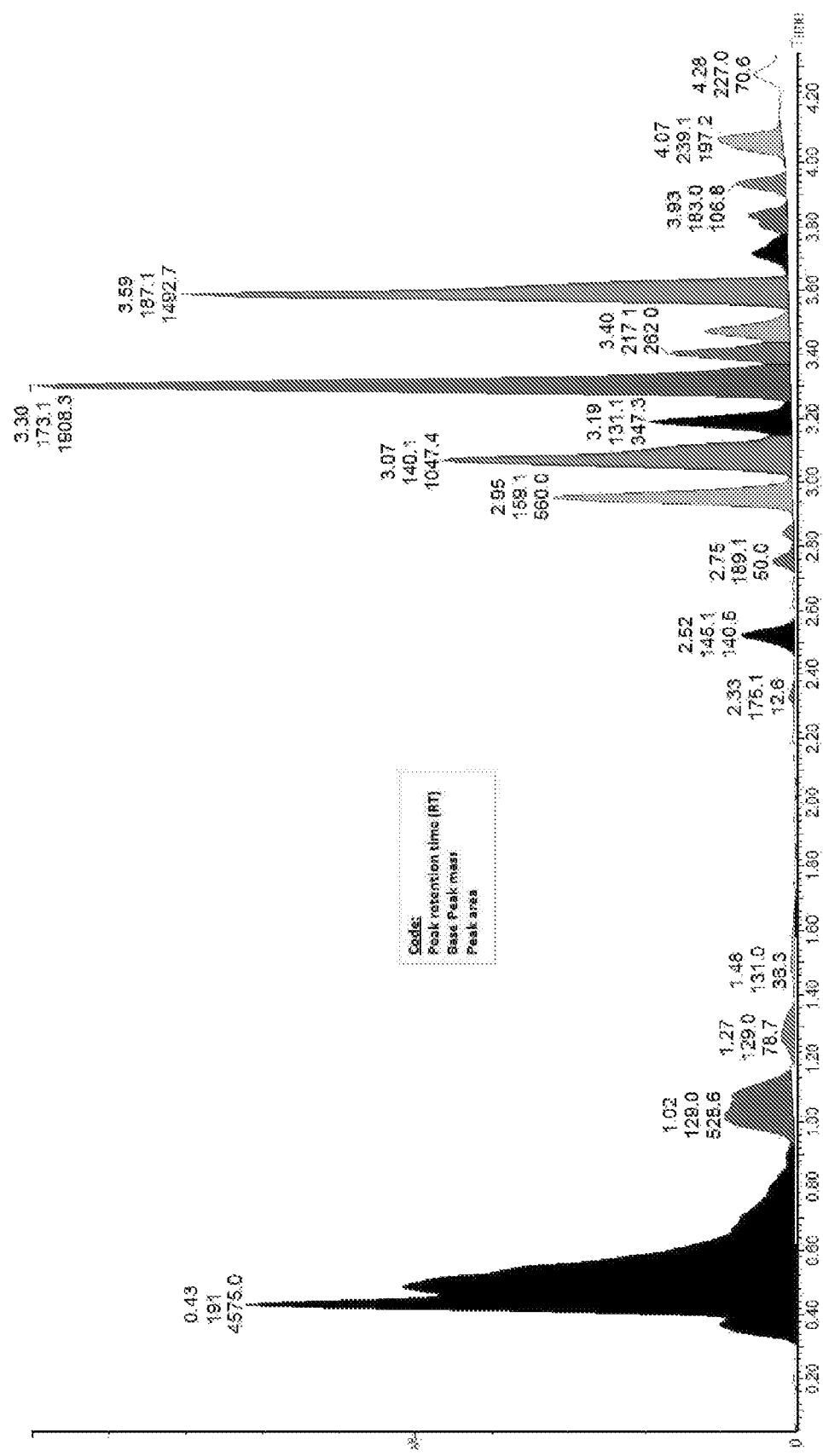
FIG. 6: depicts the integrating of the area under the peaks of FIG. 5 to aid in characterization of the sugar acid.

Product Characterization:

From the LC-MS data as shown in Table 5, FIG. 5 and FIG. 6 it is apparent that the product is composed of a wide range of small organic acids which tend to ionize better in $ESI^{-ve}$ (electrospray negative mode-loss of proton off the carboxylic acid group). The signal intensity is thus better in $ESI^{-ve}$ and software was then used to integrate all identified peaks. Each peak, represents a different compound, with unique mass-to-charge ratio (m/z), whose area is proportional to the concentration of that compound in the product. By expressing each peak area, as a percentage of the total peak area, an idea can be obtained of the percentage (%) composition of the product.

TABLE 4

Evaluation of control (% rating) of the weed species *A. hybridus, C. album, C. carinatum, T. minuta, P. oleracea, D. strumonium, D. sanguinalis* and *U. panicoides* where Roundup PowerMax ™ was applied alone or in combination with either the sugar acid of the present invention or an ammonium sulphate based adjuvant in different water hardness concentrations of $CaCl_2$, NaCl and $NaHCO_3$, respectively at 14 and 21 days after application (DAA).

| | | | | Control (%) | |
|---|---|---|---|---|---|
| Treatment | Water | Adjuvant | Rep | 14 DAA | 21 DAA |
| 1 | Distilled | — | 1 | 95 | 100 |
| 1 | Distilled | — | 2 | 98 | 100 |
| 1 | Distilled | — | 3 | 90 | 98 |
| 2 | Distilled | sugar acid | 1 | 80 | 100 |
| 2 | Distilled | sugar acid | 2 | 70 | 98 |
| 2 | Distilled | sugar acid | 3 | 80 | 100 |
| 3 | Distilled | $(NH_4)_2SO_4$ based | 1 | 90 | 100 |
| 3 | Distilled | $(NH_4)_2SO_4$ based | 2 | 90 | 100 |
| 3 | Distilled | $(NH_4)_2SO_4$ based | 3 | 80 | 100 |
| 4 | $CaCl_2$ (200) | — | 1 | 50 | 90 |
| 4 | $CaCl_2$ (200) | — | 2 | 90 | 100 |
| 4 | $CaCl_2$ (200) | — | 3 | 60 | 90 |
| 5 | $CaCl_2$ (200) | sugar acid | 1 | 50 | 98 |
| 5 | $CaCl_2$ (200) | sugar acid | 2 | 90 | 100 |
| 5 | $CaCl_2$ (200) | sugar acid | 3 | 95 | 98 |
| 6 | $CaCl_2$ (200) | $(NH_4)_2SO_4$ based | 1 | 95 | 100 |
| 6 | $CaCl_2$ (200) | $(NH_4)_2SO_4$ based | 2 | 75 | 100 |
| 6 | $CaCl_2$ (200) | $(NH_4)_2SO_4$ based | 3 | 95 | 100 |
| 7 | $CaCl_2$ (400) | — | 1 | 90 | 98 |
| 7 | $CaCl_2$ (400) | — | 2 | 85 | 98 |
| 7 | $CaCl_2$ (400) | — | 3 | 90 | 100 |
| 8 | $CaCl_2$ (400) | sugar acid | 1 | 90 | 95 |
| 8 | $CaCl_2$ (400) | sugar acid | 2 | 100 | 100 |

TABLE 4-continued

Evaluation of control (% rating) of the weed species *A. hybridus, C. album, C. carinatum, T. minuta, P. oleracea, D. strumonium, D. sanguinalis* and *U. panicoides* where Roundup PowerMax ™ was applied alone or in combination with either the sugar acid of the present invention or an ammonium sulphate based adjuvant in different water hardness concentrations of $CaCl_2$, NaCl and $NaHCO_3$, respectively at 14 and 21 days after application (DAA).

| Treatment | Water | Adjuvant | Rep | 14 DAA | 21 DAA |
|---|---|---|---|---|---|
| 8 | $CaCl_2$ (400) | sugar acid | 3 | 95 | 100 |
| 9 | $CaCl_2$ (400) | $(NH_4)_2SO_4$ based | 1 | 90 | 100 |
| 9 | $CaCl_2$ (400) | $(NH_4)_2SO_4$ based | 2 | 90 | 100 |
| 9 | $CaCl_2$ (400) | $(NH_4)_2SO_4$ based | 3 | 95 | 100 |
| 10 | $CaCl_2$ (600) | — | 1 | 80 | 98 |
| 10 | $CaCl_2$ (600) | — | 2 | 80 | 100 |
| 10 | $CaCl_2$ (600) | — | 3 | 60 | 80 |
| 11 | $CaCl_2$ (600) | sugar acid | 1 | 95 | 100 |
| 11 | $CaCl_2$ (600) | sugar acid | 2 | 80 | 98 |
| 11 | $CaCl_2$ (600) | sugar acid | 3 | 90 | 100 |
| 12 | $CaCl_2$ (600) | $(NH_4)_2SO_4$ based | 1 | 95 | 100 |
| 12 | $CaCl_2$ (600) | $(NH_4)_2SO_4$ based | 2 | 100 | 100 |
| 12 | $CaCl_2$ (600) | $(NH_4)_2SO_4$ based | 3 | 100 | 100 |
| 13 | $CaCl_2$ (800) | — | 1 | 50 | 90 |
| 13 | $CaCl_2$ (800) | — | 2 | 60 | 80 |
| 13 | $CaCl_2$ (800) | — | 3 | 50 | 90 |
| 14 | $CaCl_2$ (800) | sugar acid | 1 | 90 | 100 |
| 14 | $CaCl_2$ (800) | sugar acid | 2 | 80 | 100 |
| 14 | $CaCl_2$ (800) | sugar acid | 3 | 70 | 90 |
| 15 | $CaCl_2$ (800) | $(NH_4)_2SO_4$ based | 1 | 90 | 100 |
| 15 | $CaCl_2$ (800) | $(NH_4)_2SO_4$ based | 2 | 95 | 100 |
| 15 | $CaCl_2$ (800) | $(NH_4)_2SO_4$ based | 3 | 95 | 100 |
| 16 | NaCl (300) | — | 1 | 90 | 98 |
| 16 | NaCl (300) | — | 2 | 100 | 100 |
| 16 | NaCl (300) | — | 3 | 90 | 100 |
| 17 | NaCl (300) | sugar acid | 1 | 80 | 98 |
| 17 | NaCl (300) | sugar acid | 2 | 100 | 100 |
| 17 | NaCl (300) | sugar acid | 3 | 95 | 100 |
| 18 | NaCl (300) | $(NH_4)_2SO_4$ based | 1 | 90 | 100 |
| 18 | NaCl (300) | $(NH_4)_2SO_4$ based | 2 | 80 | 98 |
| 18 | NaCl (300) | $(NH_4)_2SO_4$ based | 3 | 95 | 100 |
| 19 | NaCl (600) | — | 1 | 95 | 100 |
| 19 | NaCl (600) | — | 2 | 95 | 100 |
| 19 | NaCl (600) | — | 3 | 90 | 100 |
| 20 | NaCl (600) | sugar acid | 1 | 100 | 100 |
| 20 | NaCl (600) | sugar acid | 2 | 75 | 98 |
| 20 | NaCl (600) | sugar acid | 3 | 95 | 100 |
| 21 | NaCl (600) | $(NH_4)_2SO_4$ based | 1 | 85 | 98 |
| 21 | NaCl (600) | $(NH_4)_2SO_4$ based | 2 | 100 | 100 |
| 21 | NaCl (600) | $(NH_4)_2SO_4$ based | 3 | 80 | 95 |
| 22 | $NaHCO_3$ (500) | — | 1 | 90 | 98 |
| 22 | $NaHCO_3$ (500) | — | 2 | 100 | 100 |
| 22 | $NaHCO_3$ (500) | — | 3 | 100 | 100 |
| 23 | $NaHCO_3$ (500) | sugar acid | 1 | 100 | 100 |
| 23 | $NaHCO_3$ (500) | sugar acid | 2 | 80 | 98 |
| 23 | $NaHCO_3$ (500) | sugar acid | 3 | 95 | 100 |
| 24 | $NaHCO_3$ (500) | $(NH_4)_2SO_4$ based | 1 | 85 | 100 |
| 24 | $NaHCO_3$ (500) | $(NH_4)_2SO_4$ based | 2 | 90 | 100 |
| 24 | $NaHCO_3$ (500) | $(NH_4)_2SO_4$ based | 3 | 95 | 100 |
| 25 | $NaHCO_3$ (1000) | — | 1 | 70 | 95 |
| 25 | $NaHCO_3$ (1000) | — | 2 | 75 | 95 |
| 25 | $NaHCO_3$ (1000) | — | 3 | 40 | 80 |
| 26 | $NaHCO_3$ (1000) | sugar acid | 1 | 100 | 100 |
| 26 | $NaHCO_3$ (1000) | sugar acid | 2 | 90 | 100 |
| 26 | $NaHCO_3$ (1000) | sugar acid | 3 | 90 | 100 |
| 27 | $NaHCO_3$ (1000) | $(NH_4)_2SO_4$ based | 1 | 95 | 100 |
| 27 | $NaHCO_3$ (1000) | $(NH_4)_2SO_4$ based | 2 | 90 | 100 |
| 27 | $NaHCO_3$ (1000) | $(NH_4)_2SO_4$ based | 3 | 95 | 100 |
| 28 | $NaHCO_3$ (1500) | — | 1 | 95 | 100 |
| 28 | $NaHCO_3$ (1500) | — | 2 | 90 | 100 |
| 28 | $NaHCO_3$ (1500) | — | 3 | 95 | 100 |
| 29 | $NaHCO_3$ (1500) | sugar acid | 1 | 85 | 95 |
| 29 | $NaHCO_3$ (1500) | sugar acid | 2 | 90 | 98 |
| 29 | $NaHCO_3$ (1500) | sugar acid | 3 | 95 | 98 |
| 30 | $NaHCO_3$ (1500) | $(NH_4)_2SO_4$ based | 1 | 90 | 98 |
| 30 | $NaHCO_3$ (1500) | $(NH_4)_2SO_4$ based | 2 | 95 | 100 |
| 30 | $NaHCO_3$ (1500) | $(NH_4)_2SO_4$ based | 3 | 95 | 98 |
| 31 | Control | — | 1 | 0 | 0 |
| 31 | Control | — | 2 | 0 | 0 |
| 31 | Control | — | 3 | 0 | 0 |

TABLE 5

Approximate compound distribution of the sugar acid product

| Peak RT | Area | m/z | % Composition |
|---|---|---|---|
| 0.435 | 4575.027 | 209 | 38.5% |
| 1.023 | 528.604 | 129 | 4.4% |
| 1.267 | 78.733 | 129 | 0.7% |
| 1.476 | 36.324 | 131 | 0.3% |
| 2.33 | 12.599 | 175 | 0.1% |
| 2.524 | 140.508 | 145 | 1.2% |
| 2.753 | 49.97 | 189 | 0.4% |
| 2.843 | 21.935 | 318 | 0.2% |
| 2.955 | 559.996 | 159 | 4.7% |
| 3.067 | 1047.436 | 140 | 8.8% |
| 3.191 | 347.274 | 131 | 2.9% |
| 3.303 | 1908.346 | 173 | 16.1% |
| 3.401 | 262.001 | 217 | 2.2% |
| 3.475 | 211.195 | 154 | 1.8% |
| 3.588 | 1492.659 | 187 | 12.6% |
| 3.712 | 119.098 | 145 | 1.0% |
| 3.839 | 122.233 | 201 | 1.0% |
| 3.928 | 106.8 | 183 | 0.9% |
| 4.07 | 197.167 | 239 | 1.7% |
| 4.277 | 70.633 | 227 | 0.6% |
| Total | 11888.54 | | 100% |

Table 5 shows that the sugar acid product described herein comprises of a reasonably heterogeneous individual compound distribution and the Inventor believes that such sugar acid products have a lower degree of hydrolyzation, relative to conventional products.

An advantage associated with the use of the novel process instead of the conventional production of sugar acids is that the novel resultant product has a lower degree of hydrolyzation, in comparison to conventional production, during said sugar acid formation.

Another advantage associated with the novel process is the large excess of un-reacted $HNO_3$ as part of the final resultant product.

Another advantage identified herein is the use of multiple heating sources being used in conjunction with each other in the apparatus for efficient heating.

A yet further advantage associated with the present product in terms of properties is the ability to act as a very strongly anionic surface agent, including the ability to associate with compounds that have strongly cationic or zwitter-ion characteristic, to form temporary chemical compounds that appear vego-friendly due to their natural origin and somewhat amino-functional character, especially when combined with phosphoro-compounds that lend towards a phospholipid generic appearance.

A still further advantage associated with the present product is that the "theoretical" HLB (hydrophylic-lipophilic balance) of the product in question is very close to 20 and therefore the product should easily flatten the angle of a water droplet in contact with a leaf or other surface.

In addition, comparing the product's HLB against that of a surfactant such as ceto-stearyl ethoxylate with 80 moles of ethylene oxide (ethoxylate), it will also quickly soften leaf-waxes and emulsify these waxes into a water phase, hence laying the leaf bare for invasion by foreign electrolytes and organic salts for a temporary period, while the leaf is wet thus enhancing the uptake and/or efficacy and/or phytotoxicity of glyphosate.

Furthermore; the product's highly anionic characteristics can also be expected to act like a sequesterant (such as EDTA—ethylene diamine tetra-acetic acid or NTA—nitrilo tri-acetic acid), and combine with metal ions to transport these through membranes and to stabilise them in soils without being washed too deeply under the soil surface.

Moreover, one can expect the product to quite easily carry both monovalent and multivalent ions such as iron, calcium, zinc, copper and manganese, because of the multivalent nature of the anionicity of the final sugar acid product as produced during the present process.

Accordingly, the invention as herein described provides numerous advantages over the prior art, in particular over conventional sugar acid processes.

Whilst only certain embodiments or examples of the instant invention have been shown in the above description, it will be readily understood by a person skilled in the art that other modifications and/or variations of the invention are possible. Such modifications and/or variations are therefore to be considered as falling within the spirit and scope of the present invention as defined herein.

The invention claimed is:

1. A composition comprising a sugar acid product obtained by a process comprising the following steps:

(i) providing, a reactor;

(ii) introducing a source of nitric acid, water and a source of starch into the reactor to form a mixture;

(iii) introducing an external heat source to the mixture to ascertain a mixture temperature of at least 70° C.;

(iv) discontinuing the external heat source once the mixture reaches about 70° C.; and (v) enabling an internal heat source in the form of an exothermic reaction to occur between the reagents for at least 2 hours;

wherein the composition further comprises glyphosate and a salt that provides cations for enhancing the uptake and/or efficacy of glyphosate.

2. The composition of claim 1, wherein the salt is $CaCl_2$.

3. The composition of claim 1, wherein at least 1 molar of un-reacted acid remains post production.

4. The composition of claim 1, wherein the nitrogen analysis of the product contains at least 6 g/kg of nitrogen.

5. The composition of claim 1, wherein at least 20% of the total added nitric acid still remains in the final product post production.

6. The composition of claim 1, wherein the product's density is 1.1194 kg/litre.

7. The composition of claim 1, wherein the product has 11.08 g/litre of nitrogen.

* * * * *